United States Patent [19]

Kung et al.

[11] Patent Number: 4,605,630
[45] Date of Patent: Aug. 12, 1986

[54] LARGE-LIPOSOME AGGLUTINATION REAGENT AND METHOD

[75] Inventors: Viola T. Kung, Menlo Park; Francis J. Martin, San Francisco; Yolanda P. Vollmer, Daly City, all of Calif.

[73] Assignee: Cooper Lipotech Inc., Menlo Park, Calif.

[21] Appl. No.: 517,826

[22] Filed: Jul. 27, 1983

[51] Int. Cl.$^4$ ............... G01N 33/544; G01N 33/571; B32B 5/16; B01J 13/00

[52] U.S. Cl. .................... 436/511; 436/528; 436/529; 436/535; 436/800; 436/805; 436/819; 436/829; 264/4.6; 428/402.2

[58] Field of Search ............. 436/511, 513, 523, 535, 436/800, 808, 819, 820, 829, 528; 252/316; 264/4.6; 428/402.2; 424/38

[56] References Cited

U.S. PATENT DOCUMENTS

| | | | |
|---|---|---|---|
| 3,949,065 | 4/1976 | Forgione | 436/511 |
| 4,342,739 | 8/1982 | Kakimi | 424/1 |
| 4,429,008 | 1/1984 | Martin | 436/829 X |
| 4,483,929 | 11/1984 | Szoka | 436/800 X |

FOREIGN PATENT DOCUMENTS

WO83/01571 5/1983 European Pat. Off. ............ 436/829

OTHER PUBLICATIONS

Daiber, A. et al, *Chemical Abstracts*, vol. 87, No. 3, 1977, p. 393, abstract #20013f.
Rao, N. V. et al, *Chemical Abstracts*, vol. 73, No. 20, 1970, p. 57, abstract #99986t.
Chan, S. W. et al, *Chemical Abstracts*, vol. 89, No. 13, 1978, pp. 366–367, abstract #103036h.
Hawley, G. G., *The Condensed Chemical Dictionary*, 10th edition, Van Nostrand Reinhold Co., N.Y., 1981, pp. 895 & 978.
Fry, J. M., Lisak, R. P., Manning, M. C., and Silberberg, D. H., *J. Immunol. Methods*, 11:185–193 (1976).
Szoka, F. Jr., and Papahadjopoulos, D., *Ann. Rev. Biophys. Bioeng.*, 9:467–508 (1980).
Szoka, F. Jr., and Papahadjopoulos, D., *Proc. Natl. Acad. Sci. USA*, 75:4194–4198 (1978).
Reeves, J. P. and Dowben, R. M., *J. Cell Physiol.*, 73:49–60 (1969).
Hub, H. H., Zimmerman, V., and Ringsdorf, H., *FEBS Letters*, 140, No. 2:254–256 (1982).
Lenk, R. P., et al., *Eur. J. Biochem.*, 121–475 (1982).
Heath, T. D., Macher, B. A., and Papahadjopoulos, D., *Biochemica et Biophysica Acta*, 640:66–81 (1981).
Martin, F. J., Hubbell, W. L., and Papahadjopoulos, D., *Biochemistry*, 20:4229–4238 (1981).
Martin, F. J. and Papahadjopoulos, D., *J. Biol. Chem.*, 257:286–288 (1982).
Smith, B. A. and McConnell, H. M., *Proc. Natl. Acad. Sci. USA*, 75:2759–2763 (1978).

*Primary Examiner*—Sidney Marantz
*Assistant Examiner*—Jeremy Jay
*Attorney, Agent, or Firm*—Ciotti & Murashige

[57] ABSTRACT

An agglutination assay reagent and method. The reagent is composed of liposomes predominantly in the 1 to 20 micron diameter size range. Each liposome has a surface array of laterally mobile ligand molecules, at a surface concentration adapted to produce reagent agglutination within about 5 minutes, when the reagent is incubated at room temperature with a multivalent ligand-binding analyte. A dye in the liposomes allows such agglutination to be visualized easily without magnification.

26 Claims, No Drawings

LARGE-LIPOSOME AGGLUTINATION REAGENT AND METHOD

BACKGROUND AND SUMMARY

The following publications are referred to by corresponding number in this application:
1. Fry, J. M., Lisak, R. P., Manning, M. C., and Silberberg, D. H., *J. Immunol. Methods* 11:185–193 (1976).
2. U.S. Pat. No. 4,342,739, issued Aug. 3, 1982 to Kakimi, F. et al.
3. Szoka, F. Jr., and Papahadjopoulos, D., *Ann. Rev. Biophys. Bioeng.* 9:467–508 (1980).
4. Szoka, F., Jr. and Papahadjopoulos, D., *Proc. Nat. Acad. Sci. USA* 75:4194–4198 (1978).
5. Reeves, J. P. and Dowben, R. M., *J. Cell Physiol.* 73:49–57 (1969).
6. Hub, H. H., Zimmerman, V., and Ringsdorf, H., *FEBS Letters* 140 No. 2:254–256 (1982).
7. Lenk, R. P., et al., *Eur. J. Biochem.* 121:475 (1982).
8. Heath, T. D., Macher, B. A. and Papahadjopoulos, D., *Biochimica et Biophysica Acta* 640:66–81 (1981).
9. Marin, F. J., Hubbell, W. L., and Papahadjopoulos, D. *Biochemistry* 20:4229–4238 (1981).
10. Martin, F. J. and Papahadjopoulos, D., *J. Biol. Chem.* 257:286–288 (1982).
11. Smith, B. A. and McConnell, H. M., *Proc. Nat. Acad. Sci. USA* 75:2759–2763 (1978).

The present invention relates to a large-liposome agglutination assay reagent, and to a method using such a reagent.

A variety of methods for determining the presence or concentration of biochemical analytes is available. The analyte to be assayed typically is one which plays an important role in biochemical processes, or is diagnostic of a particular disease state.

Several analyte-assay techniques are based on specific, high-affinity binding between the analyte to be assayed and a ligand in an assay reagent. The ligand and analyte are opposite members of a high-affinity, ligand-/anti-ligand binding pair, which may include antigen-antibody, immunoglobulin-protein A, carbohydrate-lectin, transport protein-receptor protein, biotin-avidin, hormone-hormone receptor protein, and complementary oligo-and polynucleotide strand pairs.

One general type of assay procedure which is based on specific ligand/analyte binding involves particle agglutination. In a typical agglutination assay, particles coated with ligand molecules are mixed with a multivalent ligand-binding analyte, producing visible particle clumping or aggregation, the extent of which is related to the amount of analyte present. The analyte functions to bridge ligands carried on different ligand-coated particles. Accordingly, the analyte molecules or particles each must have at least two ligand-binding sites which are arranged spatially to promote such bridging. The analyte may be either divalent, meaning it has two such binding sites, or multivalent, meaning that more than two sites are present in the molecule. The term "multivalent" will be used herein to denote analyte molecules or particles containing two or more binding sites capable of bridging ligands carried on separate agglutinatable particles.

A variety of agglutinatable particles may be used in forming an agglutination-assay reagent. For example, the Venereal Disease Research Laboratory (VDRL) test for syphilis uses an agglutination reagent composed of an emulsion of lipid droplets containing the nontreponemal lipid antigen cardiolipin. When the droplet suspension is mixed with the serum of a syphilitic subject, reagin antibody present in the serum as a result of syphilis infection reacts specifically and with high affinity to cardiolipin, producing particle agglutination.

In the VDRL test, a sample of the serum to be tested for the presence of reagin is heat-treated for 30 minutes at about 56° C., and a well-defined quantity of the heat-treated serum is placed as a droplet on the surface of a glass slide or the like. A measured quantity of the lipid suspension is added to the serum aliquot, and the reaction components are mixed by rotating the slide at about 180 rpm on a mechanical rotor. After a 4-minute mixing period, the slide is examined microscopically for evidence of emulsion-particle agglutination.

Because the cardiolipin-containing lipid emulsion is relatively unstable, it must be prepared fresh on the day of use, adding time and expense to the procedure. Preparing and heat-treating the serum sample for use in the test is also time consuming. That the reaction components must be mixed by rotation at a precise mixing speed, and that a microscope must by used for detecting the agglutination reactin also add to the inconvenience and expense of the test.

Lipid bilayer vesicles, or liposomes, have also been proposed in connection with particule-agglutination reagents. U.S. Pat. No. 4,232,001 to Jensen suggests using an estrophylin-liposome agglutination reagent for detection of anti-estrophylin antibody. A serological technique for detection of antibody to galactocerebroside using a galactocerebroside-containing liposome reagent has been described by Fry, et al. in reference 1. In this technique, heat-treated antiserum is incubated with the liposome reagent for about 1 hour, after which the reaction mixture is examined for clumps of agglutinated liposomes. The liposome reagent was prepared by a method which produces multilamellar vesicles of heterogeneous sizes ranging from about 0.05 to 20 microns in diameter.

Liposome agglutination reagents known in the prior art are characterized by relatively slow agglutination times, which may make them impractical for use in clinical testing. Many agglutination assays are conveniently performed as a droplet assay on a glass slide or the like, and evaporation losses from the droplet limit reaction times to about 10 minutes at most. In the above-referenced serological technique described by Fry, et al., for example, a serum sample was incubated with the liposome reagent in a shaking water bath for one hour. The extended reaction time may also accentuate undesired secondary reactions which affect assay results. Such reactions may include analyte instability, non-specific liposome agglutination, and complement-mediated liposome disruption.

Another limitation associated with liposome-agglutination reagents known in the prior art is the difficulty of visualizing clumps of agglutinated liposomes. Although Fry, et al. describe examining for agglutination visually, it has been the experience of the inventors that clumps of agglutinated liposomes produced in accordance with prior art methods can be identified with certainty, particularly in relatively weak agglutination reactions, only by microscopic examination.

The VDRL and liposome reagents discussed above are both composed of lipid-containing particles. Several types of rigid macromolecular particles have also been used in producing particle-agglutination reagents. For example, the Rapid Plasma Reagin (RPR) test, another non-treponemal syphilis test, employs a suspension of cardiolipin coated charcoal particles which are agglutinated in the presence of reagin antibody. The RPR teest is perfomed by mixing the charcoal suspension and the reagent sample, which may be an unheated serum or plasma sample, in a well-defined volume ratio on a plastic-coated card or the like. The card is rotated at about 100 rpm for 8 minutes to produce reagent-mediated charcoal particle agglutination. Agglutination can be determined visually, i.e. with the unaided eye.

The RPR test just described provides certain advantages over the VDRL syphilis test. The antigen-charcoal suspension is generally stable for a period of up to about a year, and thus fresh antigen suspensions need not be prepared. Sample preparation is easier, in that unheated serum or plasma samples may be used. The sample result can be read more easily and quickly since microscopic examination of the agglutination reaction is not required.

Nonetheless the RPR test has not been entirely satisfactory. The suspension and assay sample must be added together in a precisely defined volume ratio in order to maximize test sensitivity without producing false positives. This requirement increases the chance of false positive readings due to inadvertent volume-measuring errors, and requires that the technician periodically calibrate the needle used to deliver the antigen suspension. That the reaction must be rotated at a defined mixing speed for a relatively long mixing period (8 minutes) is a disadvantage as well.

Glass beads and polymeric microspheres, such as latex beads, are other types of rigid, macromolecular particles used in forming particle-agglutination reagents. Kakimi et al. have described another type of rigid-surface agglutination particle composed generally of a lipid core encased in a polymerized outer coat (reference 2). A disadvantage of these particles is that many ligands, including some lipophilic ligands, cannot be attached to glass or polymeric surfaces without significant loss in analyte-binding activity. Further, agglutination reactions involving rigid-surface agglutination particles may be relatively slow and therefore unsuitable for agglutination assays which are most conveniently performed on the surface of a glass slide or the like.

One general object of the invention, therefore, is to provide a novel large-liposome agglutination reagent which substantially overcomes above-discussed problems associated with particle-agglutination reagents known in the prior art.

A more specific object of the invention is to provide such a reagent which is adapted to produce particle agglutination, in the presence of a multivalent analyte within about 1 to 5 minutes.

Still another object of the invention is to provide such a reagent which contains a trapped dye at a concentration adapted to allow reagent agglutination to be visualized easily without magnification.

A particular object of the invention is to provide such a reagent for use in testing for syphilis.

Another particular object of the invention is to provide such a reagent for use in detecting an antigenic analyte such as hepatitis-B surface antigen.

Still another object of the invention is to provide an improved agglutination assay method which uses such a reagent.

The agglutination assay reagent of the invention includes liposomes predominantly in the 1-20 micron size range. The liposomes each contain a surface array of laterally mobile ligand molecules at a surface concentration adapted to produce reagent agglutination, within 1-5 minutes, when the reagent is incubated at room temperature with a multivalent ligand-binding analyte. In one embodiment of the invention, the reagent ligand includes cardiolipin at a lipid molar concentration of between about 1% and 20%.

The reagent also includes a dye trapped in the liposomes at a concentration adapted to allow reagent agglutination to be visualized easily without magnification. The dye may be anchored to the lipid components of the liposomes, or may be a water-soluble dye encapsulated in the liposome vesicular inner spaces. The quantity of reagent suspension which can be mixed with a given volume of analyte to produce optimal or near optimal agglutination without producing non-specific agglutination may be increased from a minimum optimal quantity, about four-fold.

An assay kit composed of a suspension of the lipid body reagent is stable for a period of up to about one year when stored under refrigeration.

These and other objects and features of the present invention will be more fully understood from the following detailed description.

DETAILED DESCRIPTION OF THE INVENTION

The present invention includes an agglutination-assay reagent for use in determining a multivalent analyte. The reagent includes liposomes predominantly in the 1 to 20 micron size range. The reagent particles in suspension are rapidly agglutinated in the presence of the analyte by virtue of specific, high affinity binding of analyte molecules or particles to laterally mobile ligand molecules carried on the surface of each liposome. A dye trapped in the liposomes allows particle agglutination to be visualized easily without magnification. Details of the invention will be described below with particular reference to methods for preparing a large-liposome agglutination reagent, and to assay procedures using the reagent. The reagent preparation methods will be described specifically with regard to methods for preparing large liposomes, for forming surface arrays of ligand molecules on the liposomes, and for entrapping dye in the liposomes.

PREPARING LARGE LIPOSOMES

As used herein, the term "liposomes" is intended to include particles whose outer surfaces are composed of lipid bilayers, formed primarily of fatty acid-containing lipids, such as phospholipids and glycolipids and/or fatty acids. The liposomes preferably include vesicles of the type having one or more lipid bilayer shells encapsulating an aqueous interior space. Vesicles having a single bilayer shell are referred to unilamellar; those having two or more bilayer shells, as multilamellar. Other lipid bilayer structures, such as non-vesicular, ribbon-like lipid bilayer structures, are also contemplated herein.

Properties of, and methods for preparing liposomes have been detailed in the literature. The reader is referred particularly to above references 3 and 4, and references cited therein, for a comprehensive discussion of the topic. What will be described herein are preferred method of preparing relatively large liposomes, and liposome properties which contribute to advantages of the invention.

Liposomes are prepared from lipid mixtures which typically include phospholipids and sterols. A list of phospholipids used commonly in liposome preparations is given on page 471 of reference 3. One consideration which determines the choice of lipids used is the degree of fluid mobility and lipid packing density which is desired in the vesicles. As reported in a number of literature reports, these characteristics can be varied according to the lengths and degree of saturation of the aliphatic chains in the lipids, and the ratio of sterol to aliphatic chain lipids used. The importance of fluid mobility in liposome surface lipids will be considered below. Packing density charcteristics are important where the surface ligands in the reagent are attached covalently to reactive surface groups in the liposomes after liposome formation. For example, it is found that the inclusion of at least about 10 mole percent of cholesterol is important for the success of certain protein-to-liposome coupling reactions.

Additionally, where the reagent is formed by covalently coupling ligand molecules to preformed liposomes, the lipid composition used in forming the vesicles is selected to produce a requisite number of reactive surface sites. Examples of lipids used in preferred coupling reactions will be discussed below.

The number and type of polar lipid groups may also be selected to produce a desired charge distribution on the lipid vesicles at a selected pH and ionic strength. The charge distribution may influence the coupling reaction used in coupling ligand molecules to the liposomes, and may be important in reducing non-specific agglutination of the reagent particles in the assay method of the invention. As will be seen below, it is generally desired to provide a moderate negative charge on the liposome surfaces, by the inclusion of negatively charged lipids at a molar concentration of up to about 20%.

A typical lipid composition used in preparing liposomes in accordance with the invention preferably includes between about 50% and 90% of a neutral phospholipid, such as phosphatidyl choline (PC), about 10% and 40% cholesterol, and between about 5% and 20% of a negatively charged lipid component. Charged lipids, such as phosphatidyl glycerol, phosphatidyl serine, phosphatidic acid, glycolipids and charged cholesterol derivatives such as cholesterol phosphate or cholesterol sulfate may be included to produce a desired surface charge in the lipid vesicles.

The lipid components used in preparing the liposomes may include lipophilic antigens or antigens covalently bound to one of the lipid components. Examples I through XII below describe the preparation and various properties of large-lipsome reagents containing the lipid antigen cardiolipin, for use in syphilis testing. Lipophilic dyes, or dyes covalently attached to one of the lipid components may also be included in the lipid mixture used in forming the liposomes, as will be described below. The antigen and/or dye included in the lipid components used in forming the liposomes may be negatively charged, and as such, may contribute all or part of the negative surface charge in the lipsomes. Example VIII below illustrates that cardiolipin included in liposomes at a molar ratio of about 7% provides an optimal or near optimal amount of negative surface charge in the cardiolipin-containing agglutination reagent.

An important finding of the present invention is that agglutination of lipid bodies coated with laterally mobile ligand molecules requires liposomes in the size range of about 1 micron or larger (Example V, Table 1) and that the extent and rate of agglutination is reduced by the addition of liposomes having diameters smaller than 1 micron (Example VI, Table 2). Accordingly, the liposome suspension used in the reagent of the invention is prepared to include a predominance of liposomes having sizes greater than about 1 micron. Preferably the suspension contains no more than about 20-25 mole percent of liposomes having sizes less than about 1 micron, and no more than about 10 percent liposomes having sizes less than about 0.6 microns in diameter.

In one general method for producing large-size liposomes, a mixture of lipids is dried to form a thin film, and the lipids are hydrated slowly to produce smaller liposomes which aggregate to form progressively larger liposomes. The size of the liposomes formed can be controlled, within limits, by varying the hydration time and amount of agitation used in hydrating the lipids. As noted in references 5 and 6, lipid vesicles having diameters of up to about 50 microns can be formed by this technique.

In another method of preparing a mixed population of relatively large unilamellar and multilamellar liposomes, referred to as reverse phase evaporation, a desired composition of lipids is dissolved in a suitable organic solvent such as diethyl ether, isopropyl ether, or a solvent mixture such as isopropyl ether and chloroform (1:1). An aqueous solution is added directly to between about 3 and 6 volumes of the lipid-solvent mixture, and the preparation is mixed, for example, by gently swirling, for a brief period to form a homogeneous emulsion. The organic solvent, or solvent mixture is removed under reduced pressure or by drying with an inert gas, resulting in the formation of a viscous, gel-like intermediate phase which spontaneously forms a vesicle dispersion when residual solvent is removed by evaporation under reduced pressure. The reader is referred particularly to references 4 and 7 for details concerning the reverse phase evaporation technique.

The reverse evaporation technique may be used to encapsulate water-soluble molecules efficiently within the interior vesicle spaces. This feature is advantageous in the present invention where the reagent is prepared to include a water-soluble dye, as in Example I.

Generally, a preparation of large liposomes formed by either of the methods just described contains a significant percentage of liposomes having diameters less than about 1 micron. These smaller liposomes can be removed preferentially by centrifuging the liposome suspension at a relatively low speed to pellet larger vesicles. The smaller liposomes in the supernatant are discarded. Alternatively, smaller vesicles can be removed by dialyzing the liposome suspension against a dialysis membrane having a defined (e.g., 1 micron) pore-size.

At the other end of the liposome-size range, liposomes having diameters of greater than about 12 to 20 microns are generally undesirable because they give a grainy appearance to the liposome reagent, which may be difficult to distinguish from a weak agglutination reaction. One simple procedure for eliminating liposomes having sizes greater than about 12 to 20 microns is to pass the suspension through a micropore filter having a defined pore size at the upper limit of desired vesicle sizes. The larger liposomes are broken down to smaller ones in this procedure, so that essentially all of the filtered liposome material is recovered.

Liposome preparations of the type described herein are generally stable for periods of up to 6 months or more when stored at refrigerator temperatures. However, over extended storage times, larger-sized liposomes, particularly unilamellar liposomes, may tend to break down spontaneously, reforming as multiple, smaller-sized liposomes. The smaller-sized liposomes may be undesirable, inasmuch as they can decrease the rate and extent of reagent agglutination. One method which may be used to minimize the liposome breakdown problem is to produce liposomes having gel-like or semirigid vesicle interior spaces which support the outer lipid shell against rupturing. Liposomes having gel-like interiors may be formed by including in the aqueous medium used in preparing the liposomes, a gel matrix material, such as agar or agarose, which can be gelled after liposome formation. Example II details a liposome-preparation technique which yields large liposomes encapsulating gelled agarose. Liposomes can be prepared to include a semirigid polymer matrix by preparing the liposomes with an aqueous polymer solution, such as a solution of acrylamide, which can be polymerized after liposome formation by known methods, such as light-induced polymerization.

FORMING LIGAND SURFACE ARRAYS ON LARGE LIPOSOMES

The reagent of the invention is prepared by forming on the surface of the large-liposome, an array of laterally mobile ligand molecules capable of binding specifically and with high affinity to multivalent analyte molecules or particle. That is, the ligand and analyte are opposite members of a binding pair of the type described above, and may include antigen-anntibody, immunoglobulin-protein A, cardiolipin-reagin, carbohydrate-lectin, biotin-avidin, hormone-hormone receptor protein, and complementary nucleotide strands. More generally, the reagent ligand molecules may include any fragment or portion of a binding-pair molecule which is capable of participating with the analyte in specific, high affinity binding. The ligand molecules may include either member of the binding pair.

Several methods are available for forming surface arrays of laterally mobile ligand molecules on the lipid-body surfaces. As indicated above, lipophilic or lipid-coupled antigen ligands may be added directly to the lipid components used in the forming of the lipid bodies. Cardiolipin is an example of a lipid antigen which can be included with the lipid components used in forming the lipid bodies, used to produce liposomes having a surface array of antibody-accessible cardiolipin molecules. Water soluble antigens which are first covalently coupled to lipid component molecules, such as phospholipid molecules, can also be incorporated directly into the lipids used in forming the lipid bodies to produce a reagent having a surface array of the ligand molecules. Chemical reaction methods for attaching various reactive groups in antigens to polar groups in lipids are well known to those skilled in the art. Examples XIII and XIV below describe liposomes having surface arrays of the dinitrophenyl phosphate (DNP) and fluoroescein isothiocyanate (FITC), respectively, formed by inclusion of antigen-lipid couples in the lipids used to form the vesicles.

Many ligands, particularly high molecular-weight biopolymers, including proteins and nucleic acids, preferably are coupled to polar, reactive head groups of lipid components contained in already-formed liposomes. Several types of reactions may be used to couple ligand molecules covalently to the polar head groups of lipids. As a general consideration, it is important to select a coupling reaction which does not significantly reduce the specific binding activity of the ligand molecules being coupled. At the same time it is advantageous to select a method which produces a relatively high coupling efficiency. Finally, care must be exercised to avoid reactions which produce significant cross linking of the surface lipid components to each other, or of the individually coupled ligand molecules to one another, since any cross linking of the reagent components (except for the individual lipid/ligand molecule conjugations) would reduce the fluid mobility of the surface lipids and attached molecules.

Without intending to limit to scope of the invention, selected methods for coupling ligand molecules covalently to liposomes will be mentioned. Reference 8 describes a coupling method which involves Schiff-base formation between an aldehyde group on the lipid or ligand molecule to be coupled, and a primary amino group on the other of the two components. The aldehyde group is preferably formed by periodate oxidation. The coupling reaction, after removal of the oxidant, is carried out in the presence of a reducing agent. Although the ligand molecules may be oxidized, more commonly it is the lipid component which is the aldehyde precursor, since periodate treatment inactivates many protein ligands. Typical aldehyde-lipid precursors include lactosylceramide, trihexosylceramide, galactocerebroside, phosphatidylglycerol, phosphatidylinositol and gangliosides.

Using large liposomes prepared by reverse phase evaporation, as described above, up to about 200 micrograms ($\mu$g) of immunoglobulin G (IgG) per micromole ($\mu$mole) of lipid vesicle lipid can be attached to the vesicle surfaces by the above method. The method has wide applicability, due to the general availability of primary amine groups in proteins and other biomolecules which can be reacted with oxidation-produced aldehydes in selected lipids.

Coupling reactions which are applicable to thiol-containing molecules may involve formation of a disulfide or thioether bond between the ligand and vesicle lipid. Such reactions are particularly useful for coupling F(ab')$_2$ and Fab' antibody fragments to lipid vesicles. In the disulfide-bond reaction, phosphatidyl ethanolamine is modified to provide a pyridyldithio derivative which can react with an exposed thiol group in a protein or other type of biomolecule. Reference 9 below gives details of the reaction. As reported in that reference, a coupling ratio of up to 600 $\mu$moles of Fab' antibody fragments per $\mu$mole of phospholipid can be achieved.

The thioether coupling method, which is described in detail in reference 10, is carried out by incorporating in the lipid vesicles a small proportion of a sulfhydryl-reactive phospholipid derivative, such as N-(4-(p-maleimidophenyl)butyryl)phosphatidyl ethanolamine (MPB-PE). The lipid vesicles are reacted with a thiol-containing protein ligand to form an essentially irreversible thioether coupling between the protein thiol group and the MPB-PE maleimide group. It is noted that the requisite protein thiol group may be endogenous to the protein or may be introduced on the protein by amino-reactive thiol reagents according to known methods. Coupling ratios of up to about 350 $\mu$grams of sulfhydryl-containing protein per μmole of lipid vesicle phospholipid have been obtained. Example XV below describes an application of this method for coupling anti-hepatitis B surface antigen (ABsAg) antibody to liposomes containing MBE-PE.

The surface concentration of ligand molecules on the liposomes is selected to produce rapid reagent particle agglutination when the reagent is mixed with the analyte to be tested. Where the ligand is a relatively small antigen, the surface concentration of ligand can be made quite great—for example, up to about 20 mole percent of the total lipid components in the liposomes. Preferred molar concentrations of cardiolipin in cardiolipin-containing liposomes used for syphilis testing are between about 1% and 20%.

As seen above, reactions capable of coupling an average of up to about 350 μg of protein per umole of lipid to liposomes are available. For proteins in the 50,000 dalton molecular weight range, and lipid vesicles in the 1 micron diameter size range, this concentration is equivalent to about $2 \times 10^5$ molecules per vesicle. This surface concentration may be several orders of magnitude greater than that required to produce rapid particle agglutination in the presence of suitable analyte molecules. Consequently, a mixture of protein ligands containing only a small percentage of specific ligand proteins can be coupled to the vesicles at a concentration sufficient to produce the requisite specific-ligand surface concentration. This feature is advantageous, for example, where the ligand molecules used in forming the reagent are contained in a crude antibody or antibody fragment preparation which may contain as little as about 0.5% antibody or antibody fragment molecules specific against the selected analyte.

PREPARING LARGE LIPOSOMES WITH ENTRAPPED DYE

The reagent also includes a dye trapped in the liposomes, at a concentration adapted to allow reagent agglutination to be visualized easily without magnification. The term "dye" as used herein is intended to include water-soluble visible or fluorescent dyes, lipid-soluble dyes or pigments, and opacifying agents.

Liposomes may have a water-soluble dye encapsulated in the aqueous interior spaces, such dyes being easily encapsulated in liposomes, in standard liposome-preparation techniques, by preparing the liposomes with an aqueous solution of the dye. The concentration of dye encapsulated in the liposomes will be substantially that of the dye in the aqueous medium used in forming the liposomes.

A number of water-soluble dyes are suitable for use in the present invention. Example I describes the preparation of a cardiolipin-coated reagent containing encapsulated erioglaucine, a dark-blue water-soluble dye. The selected concentration of encapsulated dye is preferably one which at a lower limit, permits the reagent particles to be visualized readily, and at an upper limit, allows agglutinated particles to be differentiated easily from free particles at an reagent concentration which gives optimal analyte-detection sensitivity. In studies reported in Example VII below, it was found that liposomes containing encapsulated erioglaucine, at concentrations below about 100 mM, were not intense enough in color to allow easy visualization of the agglutinated liposomes without magnification. At dye concentration significantly above 100 mM, an agglutination-reaction droplet containing the reagent is so intensely colored that only at a suboptimal reagent concentration can weak particle agglutination be detected easily.

In some reagents, it may be desired to trap the reagent dye in the lipid phase of the lipid bodies, either by using a lipophilic dye which is soluble in the lipid phase of the reagent, or a dye which is coupled covalently to one of the lipid components used in forming the reagent. Examples II and XII below describe liposomal preparations containing the lipophilic dyes Sudan IV and Sudan Black, respectively. Example XI illustrates a liposomal reagent containing a pink dye (rhodamine B) which is covalently attached to a phospholipid component in the liposomes. The surface concentration of dye which is selected is that which maximizes the ability of the agglutinated lipid bodies to be visualized without magnification, yet produces little or no effect on the agglutination properties of the lipid bodies. As will be seen in Examples XI and XII below, high surface concentrations of dyes can lead to non-specific reagent agglutination.

The importance of lipid-body size in the reagent of the invention has been mentioned above, and will become appreciated more fully from the studies reported in Examples V and VI. A second important property of the reagent is the lateral mobility of the ligand molecules on the lipid body surfaces, by which is meant the ability of surface ligands to migrate rapidly across the surface of a lipid body. This feature facilitates attachment of lipid bodies to one another in an agglutination reaction, for reasons which will now be considered.

The attachment of liposomes to solid surfaces through ligand/anti-ligand binding reactions has been discussed in two earlier patent applications entitled "Lipid-Vesicle-Surface Assay Reagent and Method", U.S. Ser. No. 452,798, and "Enhanced Agglutination Method and Kit", U.S. Ser. No. 486,793, both applications of which are assigned to the assignee of the present application. As disclosed in these two applications, stable ligand-specific binding of a liposome to a solid support appears to require multiple ligand/anti-ligand bonds between the liposome and the surface. The fluidity, or lateral mobility, of ligands on the liposome surfaces facilitates formation of multiple ligands/anti-ligand binding events by allowing ligands to migrate to binding positions within a short time following an initial binding event involving a single ligand molecule and an anti-ligand on the solid surface. Diffusion constants on the order of $10^{-11}$ to $10^{-8}$ cm$^2$/sec for phospholipid diffusion within lipid bilayers have been measured (reference 11).

The lateral mobility of the ligand molecules on liposome surfaces similarly enhances liposome agglutination in a particle-agglutination reaction. The rate of agglutination is increased because each liposome-liposome approach is more likely to produce the requisite multi-site contacts than in a reagent having rigid-position ligands. The sensitivity of the reaction is increased because analyte molecules bound to free (unagglutinated) liposomes are able to collect in localized surface regions of the liposome to promote agglutination formation through multi-site binding with other liposomes. In particles having relatively fixed ligand molecules, by contrast, a significant proportion of analyte molecules become bound to surface ligands at positions remote from areas of multi-site binding with other particles.

AGGLUTINATION ASSAY PROCEDURES

An agglutination assay method using the reagent of the invention is performed by adding a suspension of the reagent to a solution of analyte to be assayed, and mixing the two components briefly to produce particle agglutination which is detectable, without magnification, within about 5 minutes and preferably within about 2 minutes.

The analyte solution may be any suitable agglutination-reaction medium which may include a biological specimen fluid, such as serum, plasma, or urine, containing the multivalent analyte to be assayed. The pH of the reaction medium is one which is compatible with ligand/analyte binding reactions, and preferably is between about pH 5 and 9. The pH and ionic strength may be adjusted to produce moderate negative-charge repulsion between reagent particles due to negatively-charged groups in the lipid body surfaces. In the examples described herein, a reagent suspended in phosphate buffered saline (PBS), pH 7.0 to pH 7.4 is added to a serum or plasma sample to produce a final reaction medium having a pH of about 7.

Where the analyte is contained in a serum or plasma sample, it may be desirable to remove or inactivate complement which might otherwise interfere with the agglutination reaction. Reagin-antibody assays reported in Example IX below indicate that, in some serum samples at least, active complement interferes with analyte-mediated agglutination of large liposomes. One technique for inactivating serum complement involves heat treating the complement, e.g., at 56° C. for 30 minutes. This technique is used in the above-described VDRL test and also in the agglutination procedure described by Fry et al. (reference 1). Complement may also be inactivated partially by the addition of a suitable quantity of choline chloride and/or ethylene diamine tetracetic acid (EDTA). Experiments conducted in support of the present invention, and detailed in Example IX, indicate that the addition of heparin to the agglutination reaction mixture appears to provide the simplest and most effective method for minimizing complement interference with the agglutination assay.

In one typical assay protocol, a predetermined volume of analyte in serum or plasma, typically about 50 $\mu$liters, is aliquotted onto the surface of a microscope slide, plastic card or the like. Such a reaction surface which can support a drop of reaction medium is referred to generally herein as a slide. A defined quantity or reagent suspension is added to the sample drop on the slide, and the reaction mixture is then gently agitated, preferably by rocking the reaction slide or card slowly by hand for a period of between about 1 and 5 minutes and preferably at least about 2 minutes, until evidence of agglutination is seen. Heparin may also be added where complement is suspected to interfere with the reaction.

The optimal quantity of lipid-body reagent which is added to a selected quantity of analyte can be determined readily by adding increasing amounts of the reagent, typically between about 50 and 400 nanomoles (nmoles), to a selected volume of the analyte-positive sample, typically about 50 $\mu$liters. At reagent concentrations below the optimal concentration, agglutination will be relatively weak. At very high reagent concentrations, the reaction mixture may appear grainy initially, making it difficult to distinguish particle agglutination. The reagent particles may also agglutinate nonspecifically at high concentration, giving a false positive reaction when reacted with an analyte-negative sample volume. It is therefore important to test the selected optimal or near optimal quantity of particle reagent added to a given volume of analyte-negative sample to insure that the reagent concentration is below a level where non-specific agglutination can occur.

As will be seen in Example IV below, an advantageous feature of the present invention is that the quantity of reagent suspension which can be mixed with the given volume of analyte solution to produce optimal or near-optimal agglutination without producing non-specific agglutination, when mixed with the given volume of analyte solution, can be varied over about a 4-fold range. Thus, for example, where optimal or near optimal agglutination is achieved with a minimum reagent quantity of about 100 nmoles, the quantity of liposomes added to the reaction can be increased up to about 400 nmoles without producing non-specific agglutination or graininess in the reaction mixture.

Describing a typical assay procedure used in practicing the method of the invention, a defined quantity of large-liposome reagent (e.g., 100 nmoles) is added to a selected quantity of analyte-positive sample (e.g., a 50 $\mu$liter serum or plasma sample) in droplet form on the surface of a glass slide. The reaction components may be mixed briefly and spread out to cover a small circular area on the slide by means of a glass rod or the like. At the initial time of mixing, the colored reagent particles are relatively evenly dispersed throughout the solution, giving the droplet a slightly grainy, but uniform color.

The reaction mixture is then gently agitated, preferably by rocking the reaction slide or card slowly by hand for a period of between about 1 and 5 minutes, and preferably at least about 2 minutes. Usually within a reaction period of about 1 minute, slight particle agglutination is evidenced by an observed segregation of the particles into discrete aggregates which may tend to collect, or pool, in isolated areas of the reaction droplet, particularly around the edges. The extent of agglutination may be characterized by a 4-grade scale according to the following definitions: 1+, up to 25%; 2+, 25% to 50%; 3+, 50% to 75%; and 4+, 75% to 100% particle agglutination. The extent of agglutination seen at 1 minute typically is 1+ to 2+.

After a 2-minute reaction period, the droplet contains easily identified colored clumps, characteristic of an agglutination grade between about 2+ and 3+. In many cases, the extent of agglutination observed after a 2-minute reaction period will be adequate to confirm a positive agglutination reaction.

After rocking the slide manually for 2 minutes, the slide is placed in a horizontal, stationary position and the agglutination reaction is allowed to proceed for an additional 3 minutes. The extent of agglutination observed at the end of the 5-minute reaction period typically is about one grade higher than that observed at the end of the initial 2-minute period. Generally, the reaction will be complete or nearly complete after 5 minutes, as evidenced by a 4+ grade agglutination.

From the above, it can be appreciated how various objects of the invention are met. The reagent of the invention may be prepared by simple liposome preparation techniques, followed by removal of smaller-sized liposomes by centrifugation, dialysis, or the like. Ligands may be included in the lipid components used in forming the liposomes, particularly in the case of small antigen ligands, or the ligands may be attached to already-formed liposomes, at relatively high surface concentrations, by one of a number of known coupling reactions.

Similarly, the dye in the reagent may be incorporated into the liposomes during liposome preparation, either by incorporating a lipophilic dye or a dye molecule attached to a lipid component in the lipid components used in forming the liposomes, or by incorporating the dye in the aqueous medium used in forming the liposomes.

The reaction method of the invention provides a significant improvement in the rate of agglutination reaction over that achievable using prior art agglutination-assay reagents. The faster reaction rate derives both from the relatively large sizes of the liposomes, and the lateral mobility of the reagent ligands, as has been discussed. The faster reaction time provides important advantages over liposome-type agglutination reagents known in the prior art. The assay test can be done more quickly and therefore more economically in a clinical setting. The reaction can be carried out on the surface droplet without significant error in assay results due to liquid evaporation. Finally, the reaction can be completed before undesired side effects such as non-specific aggregation or analyte instability become important. Even when compared with other types of agglutinatable particles, such as the small lipid emulsion particles used in the VDRL test or the charcoal particles used in the RPR syphilis test, the reagent of the present invention produces significantly faster agglutination. As will be seen in Example X, the large-liposome reagent also provides substantially greater test sensitivity than the RPR syphilis test.

The fact that the liposome reagent can be mixed with an analyte sample in an analyte-to-reagent ratio that may vary over a 4-fold range without significantly affecting assay results reduces the possibility that the assay will be affected by volume-dispensing errors. A further simplification in the method results from the fact that the reaction card or slide need only be rocked manually for one or two minutes rather than machine-rotated at a well defined rotation speed for extended periods.

The larger liposomes also allow for easy visualization of agglutination of dye-containing lipid bodies, without magnification.

Another aspect of the invention which can be appreciated from the above is the provision of a particle-agglutination kit for determination of multivalent analytes. The kit includes a suspension of the reagent particles which is substantially stable for periods of more than about 6 months when stored at refrigerator temperatures. The kit may further include a card or slide upon which the agglutination reaction is adapted to be performed, and which provides a suitable background contrast to the reagent particles, to allow the agglutinated particles be more easily visualized.

The following examples describe particular embodiments of making and using the invention.

EXAMPLE I

Preparation of Cardiolipin-Coated Reagent

Method 1

This example describes the preparation of cardiolipin-coated liposomes predominantly in the 1 to 20 micron size range containing encapsulated erioglaucine. Phosphatidyl choline (PC) (20 $\mu$moles), cholesterol (8 $\mu$moles) and cardiolipin (2 $\mu$moles) were dissolved in 1.5 ml of ether. To this lipid mixture was added 0.3 ml of 10 mM $NaPO_4$, 10 mM NaCl, 2 mM EDTA, pH 7 (low salt buffer), containing 100 mM of erioglaucine. The mixture was sonicated in a bath sonicator during which organic solvent was evaporated by a stream of nitrogen. After sonication, the liposomes were resuspended in phosphate-buffered saline or PBS and centrifuged at 3,000×g for 5 minutes to remove small liposomes. The liposome pellets were washed twice in PBS by pelleting at 12,000×g for 10 minutes to remove dye completely. The reagent particles were resuspended in PBS to a final liposome concentration of about 20 nmoles/$\mu$liter.

Examination of the preparation by light microscopy showed that the liposomes were almost exclusively vesicular, containing predominantly multilamellar structures, and including fewer than about 20–25% vesicles of diameters less than about 1 micron.

EXAMPLE II

Preparation of Cardiolipin-Coated Reagent

Method 2

Large liposomes containing a semi-rigid agarose interior were prepared by a method similar to that described in Example I. PC (20 $\mu$moles), cholesterol (8 $\mu$moles), cardiolipin (2 $\mu$moles), and Sudan IV (0.25 mg) were dissolved in 1.5 ml of ether. Sudan IV is a lipophilic red dye which becomes entrapped in the bilayer phase of the formed liposomes. To this lipid mixture was added 0.3 ml of a 1% solution of agarose in water at room temperature. The agarose solution, which was obtained from FMC Corp. (Rockland, Me.), gels at about 15° C. and remelts at 45° C. The liposome reagent was prepared from this stage substantially as described in Example I. The distribution of liposome sizes in the reagent was substantially identical to that of the reagent of Example I, as determined by microscopic examination.

EXAMPLE III

Preparation of Cardiolipin-Coated Reagent

Method 3

The reagent-preparation methods used in Examples I and II followed the reverse phase evaporation technique described generally in references 4 and 7. The present example describes a large-liposome preparation method which has been found to yield a higher percentage of large-liposomes than that produced by the methods of Examples I and II.

PC (20 $\mu$moles), cholesterol (8 $\mu$moles), and cardiolipin (2 $\mu$moles) were dissolved in about 5 ml chloroform in a 100 ml round-bottom flask. The solvent was removed by rotary evaporation under reduced pressure, leaving a thin lipid film in the flask. A 2.5 ml solution of 100 mM erioglaucine low salt buffer was added to the flask and swirled gently over the lipid film. The lipids were allowed to swell slowly for at least 2 hours.

The resulting liposome suspension was washed twice in PBS buffer by pelleting at 3,000×g for 5 minutes to remove small liposomes, and one time at 11,000×g for 5 minutes to remove the dye completely. The large-liposome suspension was then passed through a 12 micron polycarbonate micropore filter to fragment liposomes having diameters greater than this pore size into smaller-diameter liposomes.

EXAMPLE IV

Agglutination Assay Test to Detect Reagin Antibody

Reagin antibody is a serum antibody complex which develops in individuals who have been infected with *Treponema pallidum*, and is a common serum indicator of syphilis infection. The reagin antibody complex reacts with the nontreponemal lipid antigen cardiolipin, and this forms the basis of a number of standard syphilis assays, such as the above-discussed VDRL and RPR tests. The ability of a reagin-positive serum to agglutinate the caradiolipin-coated reagent of Example I was examined. Increasing $\mu$liter amounts of the reagent, ranging from 1 $\mu$liter (20 nmoles) to 25 $\mu$liters (500 nmoles) were added to 50 $\mu$liter aliquots of reagin-positive serum on a glass slide at room temperature. The slide was rocked gently by hand for 2 minutes. After 1 minute incubation, detectable agglutination was observed in the reaction mixtures containing at least about 60 nmoles of reagent. At two minutes, a 3+ grade of agglutination was measured in the mixtures containing at least 60 nmoles reagent. After rocking the slide for 2 minutes, the reaction mixtures were incubated for another 3 minutes without moving the slide, while the agglutination reactions proceeded essentially to completion. The final agglutination reading taken at 5 minutes showed 4+ grade agglutination in the mixtures containing at least 60 nmoles reagent.

The same test was conducted with reagin-negative serum. No agglutination was observed in the reaction mixtures containing up to about 300 nmoles of reagent. The range of reagent which, when added to a given amount of sample, produces optimal agglutination without producing non-specific agglutination thus can be varied over about a five-fold range—in the present example between about 60 and 300 nmoles.

The serum sample used in this example contained reagin-antibody at a concentration which produced rapid and essentially complete reagent agglutination in a reaction mixture containing between about 60 and 300 nmoles of reagent. As will be seen in Example X below, an optimal concentration of reagent agglutinates more slowly and less extensively at lower analyte concentrations. The serum used herein was also found to produce little or no complement interference with the agglutination test.

A similar assay was also conducted using a reagin-containing plasma sample, which also gave strong agglutination when mixed with the reagent. The large-liposome reagents prepared in accordance with Example II and III were also tested with the reagin-positive serum used above. Both reagents gave strong agglutination when mixed with the serum and showed no agglutination when reacted with reagin-negative serum.

EXAMPLE V

Agglutination of Small Cardiolipin-Coated Liposomes

In this section, the minimum size range of liposomes capable of agglutinating rapidly in the presence of analyte is examined. A suspension of mixed-size multilamellar vesicles was prepared according to the method described in reference 1. PC (20 $\mu$moles), cholesterol (8 $\mu$moles) and cardiolipin (2 $\mu$moles) were dissolved in 1 ml of chloroform in a conical tube. The tube was rotated slowly while the solvent was evaporated by reduced pressure, producing a lipid film coating the walls of the bottom of the tube. After the addition of 5 ml of 100 mM erioglaucine in low salt buffer (1.0 mM NaCl, 10 mM NaPO$_4$, 2 mM EDTA), the tube was stoppered and shaken by hand for about 5 minutes. The liposome suspension was concentrated by centrifugation and resuspended to a concentration of about 20 nmoles/$\mu$liter. Microscopic examination of the liposome suspension showed a predominance of multilamellar vesicles of heterogenous sizes ranging from about 0.05 micron to 20 microns in diameter.

In an initial test, portions of the multilamellar vesicle liposome preparation were extruded through either 1.0, 0.8 or 0.6 micron polycarbonate micropore filters. Passage of the vesicles through the filters having the defined pore sizes produced suspensions of liposomes whose largest diameters were approximately equal to the size of the filter pore sizes. The four different liposome fractions are indicated in Table I, identified as non-extruded or by one of three pore sizes indicated.

The extent of agglutination produced by reacting 100 nmole amounts of each of the four multilamellar reagents with 50 $\mu$liter aliquots of reagin-positive serum was assayed as in Example IV. The extent of agglutination was determined at 2 minutes, 5 minutes and 10 minutes, with the results shown in Table I. As seen, none of the liposome preparations agglutinated within 2 minutes and only the non-extruded fraction, containing liposomes having diameters greater than about 1 micron, produced any agglutination within ten minutes of reaction time. This contrasts with the results observed in Example IV, where the large-liposome reagent of the invention showed about a 3+ grade agglutination after 2 minutes and 4+ grade agglutination after 5 minutes.

TABLE I

| | 2 min | 5 min | 10 min |
|---|---|---|---|
| non-extruded | — | 1+ (weak) | 2+-3+ |
| 1.0 micron | — | — | — |
| 0.8 micron | — | — | — |
| 0.6 micron | — | — | — |

EXAMPLE VI

Effect of Small Liposomes on Large-Liposome Reagent Agglutination

The experiment of Example V suggests that analyte-mediated liposome agglutination requires the presence of liposomes having diameters of about 1 micron or greater. The relatively weak agglutination of the non-extruded, multilamellar vesicles, when compared with the large-liposome reagent used in Example IV, further suggests that the presence of a smaller vesicles may inhibit large-liposome agglutination.

To test the effect of small liposomes on large liposome agglutination, the large-liposome reagent of in Example I was mixed with increasing amounts of one of the four multilamellar vesicle preparations from Example V, and the agglutinability of the mixed liposome population by reagin-positive serum was examined. Table II below shows the various mixed-liposome populations which were tested. As a control 5 $\mu$liters, (100 nmoles) of large-liposome reagent from Example I were mixed with 50 $\mu$liters of reagent-positive serum and reacted under conditions used in Example IV. The results shown are similar to that reported in Example IV above.

One group of mixed-size cardiolipin-coated liposomes tested included 100 nmoles of the large-liposome reagent, and 20 nmoles of one of the four multilamellar vesicle preparations from Example V. This group is indicated at 2 in Table II. As seen, the addition of progressively smaller-sized liposomes increased the reaction time required to produce a given level of agglutination, but did not significantly affect the extent of agglutination observed after 10 minutes.

The next group of mixed-size liposomes tested included 100 nmoles of the large-liposome reagent and 60 nmoles of one of the four different-sized vesicle preparations, as indicated at 3 in Table II. The extent of agglutination seen after 2 minutes was relatively weak (1+) or undetectable. The extent of agglutination observed after 5 and 10 minutes of reaction time were generally about 1 grade less than that observed for the corresponding preparations containing only 20 nmoles of the smaller-sized liposomes.

The last group of liposome samples which were tested were prepared by mixing 100 nmoles of the large liposome reagent with the same quantity of one of the four various-sized multilamellar vesicle preparations. The extent of agglutination observed is shown at 4 in Table II. Taken together, the data indicate that the presence of progressively greater quantities of progressively smaller liposomes reduces both the rate and extent of agglutination which is produced in a large-liposome reagent prepared according to the invention.

TABLE II

|  | 2 min. | 5 min. | 10 min. |
| --- | --- | --- | --- |
| 1. 100 nmoles large-liposome reagent | 3+ | 4+ | 4+ |
| 2. +20 nmoles: non-extruded | 2+ | 4+ | 4+ |
| 1.0 micron | 1+ | 3+ | 4+ |
| 0.8 micron | 1+ | 3+ | 4+ |
| 0.6 micron | 1+ (weak) | 2+ | 3+–4+ |
| 3. +60 nmoles: non-extruded | 1+ | 3+ | 4+ |
| 1.0 micron | 1+ (weak) | 2+–3+ | 3+ |
| 0.8 micron | 1+ (weak) | 2+ | 2+–3+ |
| 0.6 micron | — | 1+ | 2+ |
| 4. +100 nmoles: non-extruded | 1+ | 2+–3+ | 3+ |
| 1.0 micron | — | 1+ (weak) | 1+–2+ |
| 0.8 micron | — | 1+ (weak) | 1+–2+ |
| 0.6 micron | — | — | 1+ (weak) |

EXAMPLE VII

Effect of Erioglaucine Concentration on Reagent Agglutination

Large liposome preparations containing either 50, 100, 200, or 400 mM erioglaucine were prepared substantially in accordance with the method of Example I, but in which the aqueous medium used in forming the liposomes contained one of the four different concentrations of erioglaucine. The final concentration of each of the preparations was adjusted to 16 nmoles/μ liter. For each of the four preparations, the nmolar amount of reagent which provided optimum visualization of particle agglutination was determined by adding to a series of 50μ liter samples of reagin-positive serum, increasing μ liter amounts of each preparation. The results are shown in Table III.

TABLE III

| erioglaucine concentration (mM) | optimum reagent concentration (nmoles) |
| --- | --- |
| 50 | — |
| 100 | 144 |

TABLE III-continued

| erioglaucine concentration (mM) | optimum reagent concentration (nmoles) |
| --- | --- |
| 200 | 64 |
| 400 | 48 |

The preparation containing 50 mM erioglaucine was too weakly stained to be easily visualized, without magnification, even at high reagent concentrations. The data for the other three preparations examined suggest that the amount of liposome reagent required to produce visualizable agglutination is roughly proportional to the concentration of dye trapped in the liposomes. However, with the 200 mM and 400 mM erioglaucine reagents, agglutination could be detected easily only at relatively low reagent concentrations, due to the increased opacity of these reagents in solution. As a consequence, the sensitivity of these reagents, in terms of minimum detectable reagin levels, was less than that of the reagent containing 100 mM erioglaucine. Thus the optimum erioglaucine concentration which optimizes both detectability and test sensitivity is about 100 mM.

EXAMPLE VIII

Effect of Charge on Reagent Agglutination

This section examines the effect of surface charge on the agglutination characteristics of a cardiolipin-containing large-liposome preparation. Four reagents, prepared using the umolar amounts of PC, phosphotidyl glyceride (PG), cardiolipin and cholesterol shown in Table IV were prepared as in Example I. Cardiolipin has a double-negative charge, and thus contributes about 13 mole percent negative charge to each reagent. PG has a single negative charge and contributes approximately 7, 17 and 33 mole percent negative charge to reagents 2, 3 and 4 respectively. Reagent 1 gave a strong reaction with positive serum and no reaction with negative serum, similar to what was found in Example IV. Reagents 2–4, however, all agglutinated when reacted with reagin-negative serum, the extent of non-specific agglutination being greater in the reagents having greater surface charge. Thus the optimal molar concentration of negatively charged lipid, based on a single charge per lipid component, is less than about 20%.

TABLE IV

| Reagent | PC | PG | Cholesterol | Cardiolipin |
| --- | --- | --- | --- | --- |
| 1 | 20 | 0 | 8 | 2 |
| 2 | 18 | 2 | 8 | 2 |
| 3 | 15 | 5 | 8 | 2 |
| 4 | 10 | 10 | 8 | 2 |

EXAMPLE IX

Complement Inactivation in Reagin-Antibody Assays

Many reagin-containing serum samples, including those tested in the examples above, produced about the same degree of agglutination whether or not the samples had first been heat-treated in inactivate serum complement. That is, active complement does not appear to interfere with large-liposome agglutination in these samples. Other serum samples, however, showed markedly higher agglutination titers when the sample assayed had been heated to inactivate complement. This example presents data on several serum samples in which complement interference with large-liposome agglutination was observed, and shows a preferred method for minimizing this complement effect.

A panel of reagin-positive samples, numbers 6057, 6061, 6060 and 6063, were obtained from the Biological Corporation of America (Palo Alto, CA) (BCA). Reagin-positive and weak reagin-positive control serum samples were obtained from Sylvana (Grand Island, NY). These samples are listed in the left in Table V below. For each sample, four different assays were carried out, each substantially in accordance with the procedure described in Example IV. The first series of assays was performed by mixing 50$\mu$ liters of non heat-treated serum samples each with about 200 nmoles of the liposome reagent from Example I. The extent of agglutination produced, after a 3 minute reaction period, is shown for each of the samples in the "not treated" column of Table V.

In a second series of assays, each serum sample was heated at 56° C. for 30 minutes to inactivate complement. The heat-treated serum was then assayed as above for reagin antibody. The extent of agglutination observed after 3 minutes is shown in the "heat-treated" column in the table. The results show increased agglutination for all of the BCA samples after heat treatment.

The RPR reagin antibody test discussed above employs a mixture of choline chloride plus EDTA in the reaction medium to inactivate serum complement. In preliminary experiments conducted in support of the present application, it was found that choline chloride reduced complement interference of liposome agglutination, bt that EDTA, at test concentrations up to 100 mM did not. The combination of choline chloride plus EDTA was less effective in inactivating complement than choline chloride alone. The third series of assays was designed using these findings: a 50$\mu$ liter aliquot of each serum sample (not heated) was mixed with 200 nmoles of liposome reagent and 2$\mu$ liters of choline chloride (20% w/v). The extent of agglutination produced after three minutes is shown for the several samples in the "plus choline chloride" column in Table V. As seen from the data, adding choline chloride was generally less effective in reducing complement interference of reagent agglutination than was heat-treating the samples.

In a final series of assays, the effect of heparin on complement inactivation was examined. In each test, 50$\mu$ liters of serum sample (not heated) and 40 $\mu$liters of heparin (1% solution of ammonium heparin) were mixed on a glass with 200 nmoles of reagent. The "plus heparin" column in Table V shows the degree of agglutination observed after a 3 minute test period. As seen, in all of the samples except BCA 6060, adding heparin to the samples was as effective or more so in inactivating complement as heat-treating the serum samples.

TABLE V

| serum | not treated | heat treated | + choline chloride | + heparin |
|---|---|---|---|---|
| BCA 6057 | neg | 1+ w | 1+ w | 3+ |
| BCA 6061 | 2+ | 4+ | 2+ | 4+ |
| BCA 6060 | neg | 2-3+ | 1+ w | 2+ |
| Sylvana, pos control | 4+ | 4+ | 4+ | 4+ |
| Sylvana, weak pos.control | 1+ w | 1-2+ | 1+ w | 1-2+ |
| BCA 6030 | neg | 3+ | 2+ | 3+ |
| negative | neg | neg | neg | neg |

The results above suggest that serum or plasma complement can be inactivated most easily and effectively in the agglutination assay of the invention by the addition of heparin to the assay reaction medium.

EXAMPLE X

Assay Sensitivity

In the present example, the sensitivity of the cardiolipin-containing reagent of Example I in detecting reagent anitbodies is compared with that of the above-described RPR reagent-antibody test.

An RPR test kit was obtained from Hynson, Westcott and Dunning (Baltimore, MD). VDRL reaction control serum (reagin-positive serum) was obtained from Sylvana (Grand Island, NY). The serum was diluted serially with saline as indicated in the column at the left is Table VI below.

The large-liposome assays were conducted substantially as described in Example IV. A 50$\mu$ liter aliquot of each of the different-dilution samples was mixed on a glass slide with 200 nmoles of the reagent from Example I. The reaction was carried out as in Example IV, the agglutination grade being read at 3 and 8 minutes. The two middle columns in the table show the results obtained. The data indicate that as the concentration of analyte decreases, reagent agglutination occurs more slowly and to a lesser extent.

TABLE VI

| | large-liposomes | | RPR |
|---|---|---|---|
| serum dilution | (3 min.) | (8 min.) | (8 min.) |
| 1:1 | 4+ | 4+ | 4+ |
| 1:2 | 4+ | 4+ | 3+ |
| 1:4 | 1+ | 3+ | neg |
| 1:8 | 1+w | 1+ | neg |
| 1:16 | neg | neg | neg |

The RPR test was performed in accordance with the instructions accompanying the RPR test kit. Agglutination was read after an 8 minute reaction period, during which the reaction mixture was rotated at about 100 rpm. The extent of agglutination observed is recorded at the right hand column in Table VI. Comparison of the two test shows that (1) after a 3-minute reaction period, the extent of agglutination produced by the method of the present invention was equal to or greater than that produced by the RPR test kit after 8 minutes and (2) the minimum concentration of reagent antibody detectable by the large-liposome reagent is about ¼ that detectable by the RPR test kit.

EXAMPLE XI

Preparation of Cardiolipid-Containing Liposomes with a Surface Bound Dye

This example illustrates the preparation of a large-liposome reagent having a surface-bound, lipophilic dye. The dye used, rhodamine-B, is a pink dye having an extinction coefficient of about 72,000 at its maximum absorbance wavelength of about 543 mm. The dye was obtained as a rhodamine-phospholipid complex, specifically N-(lissamine rhodamine B sulfonyl)-dioleoyl phosphatidyl ethanolamine (molecular weight, 1,277 daltons), from Avanti Polar Lipids (Birmingham, AL). Three reagents, each containing essentially the same quantities of PC, cholesterol, and cardiolipin as in Example I, and either 0.016$\mu$ moles of rhodamine-PE (reagent 1), 0.078$\mu$ moles of rhodamine-PE (reagent 2) or 0.390μ moles of rhodamine-PE (reagent 3) were prepared in accordance with Example I, except that erioglaucine was omitted. Reagent 1 was too pale to enhance agglutination detectability.

Reagents 2 and 3 were each used in a reagin-antibody assay of the type described in Example IV. The data, which are presented in Table VII below, show that reagent 2 produced a strong specific agglutination, after a 2-minute reaction period at the two different reagent concentrations used, and produced no agglutination when mixed with control serum. Reagent 3, containing the highest concentration of surface dye, reacted even more strongly with reagin-positive serum, after a 2-minute incubation period, but also showed a weak non-specific agglutination when mixed with control serum. Thus, the optimal concentration of the dye, exemplified by reagent 2, is one which produces an intense enough color to enhance agglutination detectability, but which is below the concentration where non-specific agglutination is observed.

TABLE VII

| Concentration (nmoles) | Serum | Agglutination (after 2 minutes) |
| --- | --- | --- |
| Reagent 2 | | |
| 120 | + | 2+ |
| 180 | + | 3+ |
| 180 | − | − |
| Reagent 3 | | |
| 85 | + | 4+ |
| 136 | + | 3+ |
| 136 | − | 1+ (weak) |

EXAMPLE XII

Preparation of Cardiolipin-Containing Vesicles Having Sudan Black Dye

Example XI above illustrates a reagent having a surface dye which is anchored to the lipid bodies through covalent attachment to a lipid component in the lipid bodies. Alternatively, a lipophilic dye may be trapped or anchored directly in the lipid phase of the reagent lipid bodies. The lipophilic dye Sudan Black B was included at various concentrations in the lipid components used to prepare cardiolipin-containing lipid body reagents in accordance with Example I. Specifically, a lipid-in-solvent mixture used to prepare the reagents included, in addition to the same quantities of the same lipids used in Example I, 0.22μ moles of alpha-tocopherol and either 50 micrograms (μg), 200 μg, 500 μg, or 1 mg of Sudan Black B. Alpha-tocopherol was added to inhibit lipid oxidation and had no measurable effect on lipid-body agglutination. The reagent containing the lowest concentration of Sudan Black B (50 μg) was not intense enough in color to enhance agglutination detectability. The two reagents having the greatest dye concentration (500 μg and 1 mg) agglutinated nonspecifically when mixed with reagin-negative serum, similar to what was observed in Example XI for the reagent containing the highest concentration of rhodamine. The reagent containing 200 μg of of dye gave strong positive agglutination when mixed with reagin-positive serum, and a negative reaction when mixed with negative serum.

EXAMPLE XIII

Preparation of Large Liposomes for Detection of Anti-DNP Antibodies

The present example describes large-liposome agglutination reagents containing the hapten dinitrophenyl phosphate (DNP). The antigen was attached to lipid vesicles surfaces by including a DNP-lipid complex in the lipid components used in forming the liposomes. DNP-PE was obtained from Avanti Polar Lipids (Birmingham, AL). Each reagent contained PC (20μ moles) PG (4μ moles), cholesterol (8μ moles) and alpha-tocopherol (0.022). In addition, reagent 1 contained 0.4μ moles of DNP-PE and reagent 2, 1.0μ moles of DNP-PE. The reagents were prepared by the reverse evaporation phase method described in Example I, and contained 100 mM encapsulated erioiglaucine.

A purified preparation of rabbit antibodies, prepared against a DNP-bovine serum albumin (BSA) conjugate, containing an estimated 1.4 mg/ml anti-DNP antibodies, was obtained from Miles Laboratories (Elkhart, IN). Agglutination assays were conducted substantially as described in Example IV. Briefly, 50μ liter aliquots of anti-DNP antiserum were mixed with increasing quantities of each of two large-liposome reagents. The reaction mixtures were rocked gently by hand for 2 minutes. Both reagents showed strong agglutination by anti-DNP antiserum within 2 minutes. Neither reagent agglutinated non-specifically when reacted with either BSA or control non-immune rabbit serum.

EXAMPLE XIV

Preparation of Large-Liposome Reagent for Detection of Anti-Fluorescein Antibodies Fluorescein isothiocyanate (FITC) was reacted with PE, under known conditions, to produce FITC-PE. Two FITC-containing reagents were prepared as in Example XIII above, substituting in one reagent, 0.1μ moles FITC-PE for 0.4μ moles of DNP-PE used in Example XIII, and in the second reagent, 0.15μ moles FITC-PE for 1.0μ moles DNP-PE.

Rabbit anti-FITC antiserum, containing an estimated 1% to 3% antibodies specific against FITC, was obtained from rabbits immunized with an FITC-BSA conjugate and Freund's adjuvant. Agglutination assays were performed by mixing 50μ liter aliquots of the antiserum with increasing quantities of each of the two fluorescein reagents, under the reaction conditions described in Example IV. Both reagents showed strong agglutination with anti-FITC antiserum, but neither agglutinated non-specifically when mixed with BSA or rabbit control serum.

EXAMPLE XV

Preparation of Large-Liposome Reagent for Detection of Hepatitis B Surface Antigen Hepatitis B surface antigen (HBsAg) is a multivalent antigen found in the serum of patients with hepatitis. Two large-liposome reagents adapted to agglutinate in the presence of HBsAg were prepared as follows: Initially, two large-liposomes suspensions were formed substantially according to the reverse-evaporation phase technique described in Example I. One suspension contained PC (20μ moles), cholesterol (8μ moles) and 2μ moles of MPB-PE, a negatively-charged phospholipid which is reactive toward thiol-containing ligand molecules. A second suspension contained PC (18μ moles), PG (2μ moles) and the quantities of cholesterol and MPB-PE used in forming the first suspension. The two suspensions were prepared to include 100 mM encapsulated erioglaucine.

Mouse monoclonal antibody against HBsAg was purified by protein-A-sepharose column chromatography. The purified antibody was thiolated with an 18-fold molar excess of N-succinimidyl 3-(3-pyridyldithio)-propionate (SPDP) for 20 minutes at room temperature, according to the method reported in reference 10. The reaction produced an average degree of thiolation of about 5.3 SH groups per antibody molecule. The thiolated antibody was reduced with dithiothreitol at pH 4.8 prior to conjugation with the liposome suspensions.

The thiolated antibody was reacted with each of the large-liposome suspensions in 10 mM NaPO4, 10 mM NaCl, and 2 mM EDTA at pH 6.8 at room temperature overnight. Each reaction mixture contained about 0.1 mg protein per μ mole lipid. After completion of the conjugation reaction, the protein-coated liposomes were freed of unbound protein by pelleting at 17,000 rpm for 15 minutes. The pelleted reagents were resuspended in PBS to a final concentration of about 20 nmoles/μ liter.

The analytes tested were purified HBsAg, subtypes adw2, awy2 and plasma antigen, all having known titers. In addition, 7 HBsAg-positive plasmas with unknown titers, obtained from Nor-Cal Biologics, Inc. (Sacramento, CA), were tested. For each reagent, increasing of μ liter quantities of reagent were added to 50μ liter aliquots of each of the ten samples tested. The three samples with known titers all showed strong agglutination with both reagents after a 2-minute incubation period. Among the seven HBsAg-positive samples obtained from Nor-Cal Biologics, five showed weakly positive reactions with both of the liposome preparations after 2 minutes, and relatively strong agglutination after 5 minutes. No agglutination with negative plasma or serum was observed.

The present example illustrates a large lipid-body agglutination reagent containing surface-attached antibody ligand molecules. Other examples herein illustrate large lipid-body reagents containing lipophilic and water-soluble surface antigen ligands. It will be apparent to those skilled in the art that a variety of ligands, including proteins, nucleic acid fragments, and small molecular-weight antigens can be used in forming large lipid-body reagents according to the teachings of the invention for use in determining corresponding anti-ligand analytes.

What is claimed is:

1. An agglutination assay reagent comprising
liposomes prepared by forming a dispersion of lipid vesicles having heterogeneous sizes both less than and greater than 1 micron, and treating the dispersion to remove vesicles whose sizes are less than about 1 micron,
each liposome having a surface array of ligand molecules at a surface concentration effective to produce liposome agglutination within about 5 minutes, when the reagent is incubated at room temperature with a multivalent ligand-binding analyte on a slide, and
a dye trapped by the liposomes at a concentration effective to allow said agglutination to be visualized directly without magnification on a slide.

2. The reagent of claim 1, wherein the liposomes are predominantly in the 1 to 12 micron size range, and the percentage of liposomes having diameters less than about 1 micron is less than about 25%.

3. The reagent of claim 1, wherein the ligand is cardiolipin contained in the lipid phase of the liposomes, at a molar concentration of between about 1% and 20%.

4. The reagent of claim 1, wherein the interior spaces of liposomes are substantially filled with a semi-rigid gel or a polymerized matrix.

5. The reagent of claim 4, wherein the semi-rigid gel includes agar or agarose.

6. An agglutination assay reagent for determination of serum or plasma reagin antibody comprising
liposomes containing cardiolipin at a molar concentration between about 1 and 20% and prepared by (a) forming a dispersion of lipid vesicles having heterogeneous sizes both less than and greater than 1 micron, and (b) treating the dispersion to remove vesicles whose sizes are less than about 1 micron, wherein incubation of the liposomes in the presence of reagin antibody at room temperature for 5 minutes is effective to produce liposome liposome agglutination on a slide, and
a dye trapped by the liposomes at a concentration effective to allow said liposomes to be visualized directly without magnification on a slide.

7. The reagent of claim 6, wherein the dye is encapsulated with the interior spaces of the liposomes.

8. The reagent of claim 7, wherein dye is carried on the liposome outer surfaces.

9. A rapid agglutination assay method for determination of a multivalent ligand-binding analyte, said method comprising
providing a suspension of liposomes (a) prepared by forming a dispersion of lipid vesicles having heterogeneous sizes both less than and greater than 1 micron, and treating the dispersion to remove vesicles whose sizes are less than about 1 micron, and (b) having a surface array of ligand molecules and a trapped dye, and
mixing the suspension with the analyte on a slide to produce liposome agglutination which is readily detectable, without magnification, within about five minutes at room temperature.

10. The method of claim 9, wherein liposomes having diameters below about 1 micron are removed by centrifugation.

11. The method of claim 9, for use in determining reagin antibody, wherein the liposomes are prepared to include between about 1 and 20 mole percent cardiolipin.

12. The method of claim 9 wherein said preparing includes forming said liposomes to encapsulate as aqueous fluid material which can be gelled or polymerized after liposome formation.

13. The method of claim 12, wherein the aqueous fluid material includes agar or agarose.

14. The method of claim 9, for use in determining a multivalent antigen, wherein the ligand includes anti-ligand antibodies covalently attached to surface lipid components in the vesicles.

15. The method of claim 14, for determination of hepatitis B surface antigen, wherein the antibodies include anti-hepatitis B surface antigen antibodies.

16. A rapid-agglutination assay method for determination of reagin antibody comprising providing a suspension of reagent particles composed of liposomes containing cardiolipin at a molar concentration between about 1%–20% and a trapped dye and prepared by (a) forming a dispersion of lipid vesicles both having heterogeneous sizes less than and greater than 1 micron, and (b) treating the dispersion to remove vesicles whose size is less than about 1 micron, and mixing the reagent with a sample of the antibody to produce agglutination which is readily detectable, without magnification, after 2 to 5 minutes at room temperature.

17. The method of claim 16, wherein the liposomes contain phosphatidyl choline, cardiolipin and cholesterol at a molar ratio of about 10:1:4.

18. The method of claim 16, which further includes adding heparin to the reagent/sample mixture.

19. In an assay procedure which includes reacting multivalent ligand-binding molecules with a suspension of ligand-coated liposomes having heterogeneous sizes both greater and less than about 1 micron, to produce liposome agglutination in proportion to the concentration of ligand-binding molecules, the improvement comprising: enhancing the rate and extent of liposome agglutination by treating the liposome suspension to remove liposomes whose sizes are less than about 1 micron.

20. The method of claim 19, wherein the treated liposome suspension contains less than about 25% of liposomes having diameters of less than about 1 micron.

21. The method of claim 19, wherein the liposome population is produced by preparing a suspension of heterogeneous-sized liposomes, and removing liposomes whose sizes are less than about 1.0 microns preferentially by centrifugation.

22. The method of claim 19, wherein the lipids are prepared to include a trapped dye, at a concentration thereof which allos agglutinated liposomes in such population to be visualized readily without magnification.

23. An agglutination assay reagent comprising liposomes predominantly in the 1–20 micron size range, wherein the interior liposome spaces are substantially filled with a semi-rigid gel or a polymerized matrix, each liposome having a surface array of ligand molecules at a surface concentration effective to produce liposome agglutination within about 5 minutes, when the reagent is incubated at room temperature with a multivalent ligand-binding analyte on a slide, and a dye trapped by the liposomes at a concentration adapted to allow such agglutination to be visualized readily without magnification on a slide.

24. The reagent of claim 23, wherein the semi-rigid gel includes agar or agarose.

25. A rapid agglutination assay method for determination of a multivalent ligand-binding analyte, said method comprising providing a suspension of reagent particles composed of liposomes primarily in the 1–20 micron size range, each liposome having a surface array of ligand molecules and a trapped dye, wherein the interior liposome spaces are substantially filled with a semi-rigid gel or polymerized matrix, and mixing the suspension with the analyte on a slide to produce particle agglutination which is readily detectable, without magnification, within about 5 minutes at room temperature.

26. The method of claim 25, wherein the semi-rigid gel includes agar or agarose.

* * * * *